United States Patent [19]

Rath et al.

[11] Patent Number: 5,230,996

[45] Date of Patent: Jul. 27, 1993

[54] USE OF ASCORBATE AND TRANEXAMIC ACID SOLUTION FOR ORGAN AND BLOOD VESSEL TREATMENT PRIOR TO TRANSPLANTATION

[75] Inventors: Matthias W. Rath, Kirchberg/Murr, Fed. Rep. of Germany; Linus C. Pauling, Big Sur, Calif.

[73] Assignee: Therapy 2000, Palo Alto, Calif.

[21] Appl. No.: 556,968

[22] Filed: Jul. 24, 1990

Related U.S. Application Data

[63] Continuation-in-part of Ser. No. 533,129, Jun. 4, 1990, abandoned.

[51] Int. Cl.$^5$ .................... A01N 1/02; A01N 43/08; A01N 33/02
[52] U.S. Cl. ........................................ 435/1; 514/474; 514/659
[58] Field of Search ........................................ 435/1, 2

[56] References Cited

U.S. PATENT DOCUMENTS 4,443,546 4/1984 Stemerman .................... 435/240

OTHER PUBLICATIONS

Krystal, G, Arthritis Rheum. 25:318-25 (1982).
Kurokawa, Y, Tohoku J. Ex. Med. 134:183-93 (1981).
Feng, J., In Vitro 13:91-99 (1977).
Malemud, C, Connect Tissue Res 6:171-9 (1978).
Hinrichs U, Arzneimittelforschung 33:143-9 (1983).
Risley, M, Biol Reprod. 36:985-97 (1987).
Popov I, Z. Exp. Chir. Transplant Kunstliche Organe 22:22-6 (1989).
Schiff, L, In Vitro 16:893-906 (1980).
Vinograd-Finkel, F, Otkrytiya, Izobret., Prom. Obraztsy, Tovarnye Znaki 49:264 (1972).
Rath, M. & L. Pauling, "Solution of the puzzle of human cardiovascular disease: Its primary cause is ascorbate deficiency, leading to the deposition of lipoprotein(a) and fibrinogen/fibrin in the vascular wall," J. Orthomolecular Med. (In Press 1991).
Markwardt, F. & H. P. Klocking, "Chemical control of hyperfibrinolytic states by synthetic inhibitors of fibrinolytic enzymes," Biomed. Biochim. Acta 42:725-730 (1983).
Werb, Z. et al., "Endogenous activation of latent collagenase by rheumatoid synovial cells," New England J. Med 296(18):1017-1023 (1977).
Knox, E. G., "Ischaemic-heart-disease mortality and dietary intake of calcium," Lancet, i, pp. 1465-1467, Jun. 30, 1973.
Berg, K. "A new serum type system in man—The Lp system," Acta Path. 59:369-382 (1963).
McLean, J. et al., "cDNA sequence of human apolipoprotein(a) is homologous to plasminogen," Nature 300:132-137 (1987).
Salonen, E-M, et al., "Lipoprotein(a) binds to fibronectin and has serine proteinase activity capable of cleaving it," EMBO J. 8(13):4035-4040 (1989).
Harpel, P. C. et al., "Plasmin catalyzes binding of lipoprotein(a) to immobilized fibrinogen and fibrin," Proc. Natl. Acad. Sci. USA 86:3847-3851 (1989).
Gonzalez-Gronow, M. et al., "Further characterization of the cellular plasminogen biding site: Evidence that Plasminogen 2 and Lipoprotein a compete for the same site," Biochemistry 28:2374-2377 (1989).

(List continued on next page.)

Primary Examiner—Douglas W. Robinson
Assistant Examiner—S. Saucier
Attorney, Agent, or Firm—George C. Limbach

[57] ABSTRACT

A method and pharmaceutical agent are provided for the prevention and treatment of cardiovascular disease, particularly cardiovascular disease in the context of diabetic angiopathy, by-pass surgery, organ transplantation, and hemodialysis, by administering ascorbate and substances that inhibit the binding of lipoprotein (a) to blood vessel walls. The use of ascorbate and lipoprotein (a) binding inhibitors such as tranexamic acid in a temporary storage solution for blood vessels and organs prior to transplantation is also demonstrated.

8 Claims, 5 Drawing Sheets

OTHER PUBLICATIONS

Hajjar, K. A. et al., "Lipoprotein(a) modulation of endothelial cell surface fibrinolysis and its potential role in atherosclerosis" Nature 339:303–305 (1989).

Armstrong, V. W. et al., "The association between serum Lp(a) concentrations and angiographically assessed coronary atherosclerosis"; Atherosclerosis 62:249–257 (1986).

Dahlen, G. H., et al., "Association of levels of lipoprotein Lp(a), plasma lipids, and other lipoproteins with coronary artery disease documented by angiography," Circulation 74(4):758–765 (1986).

Miles, L. A. et al., "A potential basis for the thrombotic risks associated with Lipoprotein (a)," Nature 339:301–302 (1989).

Zenker, G. et al., "Lipoprotein(a) as a strong indicator for cerebrovascular disease," Stroke 17(5)942–945 (1986).

Zechner, R. et al., "Fluctuations of plasma Lipoprotein-A concentrations during pregnancy and post partum," Metabolism 35(4):333–336 (1986).

Hoff, H. et al., "Serum Lp(a) level as a predictor of vein graft stenosis after coronary artery bypass surgery in patients," Circulation 77(6):1238–1244 (1988).

Rath, M. et al., "Detection and quantification of Lipoprotein(a) in the arterial wall of 107 coronary bypass patients," Arteriosclerosis 9(5):579–592 (1989).

Cushing, G. L. et al., "Quantitation and localization of Apolipoproteins [a] and B in Coronary artery bypass vein grafts resected at re-operation," Arteriosclerosis 9(5):593–603 (1989).

Bruckert, E. et al., "Increased serum levels of Lipoprotein(a) in diabetes mellitus and their reduction with glycemic control," JAMA 263(1):35–36 (1990).

Blumberg, B., et al., "A human lipoprotein polymorphism," J. Clin. Invest. 41:1936–1944 (1962).

Eaton, D. L., et al., "Partial amoni acid sequence of apolipoprotein(a) shows that it is homologous to plasminogen," Proc. Natl. Acad. Sci. USA, 84:3224–3228 (1987).

Wright, L. C. et al., "Elevated apolipoprotein(a) levels in cancer patients," Int. J. Cancer 43:241–244 (1989).

Som, S. et al., "Ascorbic acid metabolism in diabetes mellitus," Metabolism 30:572–577 (1981).

Maeda, S. et al., "Transient changes in serum liproprotein(a) as an acute phase protein," Atherosclerosis 78:145–150 (1989).

Kapeghian, J. C. et al., "The effects of glucose on ascorbic acid uptake in heart endothelial cells: Possible pathogenesis of diabetic angiopathies," Life Sci. 34:577 (1984).

Tomlinson, J. E. et al., "Rhesus monkey apolipoprotein(a," J. Biol. Chem. 264:5957–5965 (1989).

Ginter, E. et al., "The effect of chronic hypovitaminosis C on the metabolism of cholesterol and athergenesis in guinea pigs," J. Atherosclerosis Res. 10:341–352 (1969).

Potential Mechanism of Ascorbate in the Binding of Lp(a) to the Arterial Wall

USE OF ASCORBATE AND TRANEXAMIC ACID SOLUTION FOR ORGAN AND BLOOD VESSEL TREATMENT PRIOR TO TRANSPLANTATION

This application is a continuation-in-part of application Ser. No. 07/533,129, filed Jun. 4, 1990, now abandoned.

TECHNICAL FIELD

The present invention relates generally to the prevention and treatment of cardiovascular disease arising as a complication from surgery or a pre-existing, unrelated disease, and more particularly to methods and compounds for that inhibit the binding of lipoprotein (a) to components of the arterial wall.

BACKGROUND OF THE INVENTION

Lipoprotein (a) ("Lp(a)") was first identified by Blumberg, B. S., et al. (1962) J. Clin. Invest. 41: 1936-1944 and Berg, K. (1963) Acta Pathol. 59: 369-382. The structure of Lp(a) resembles that of low-density lipoprotein ("LDL") in that both share a lipid-/apoprotein composition, mainly apolipoprotein B-100 ("apo B"), the ligand by which LDL binds to the LDL receptors present on the interior surfaces of arterial walls. The unique feature of Lp(a) is an additional glycoprotein, designated apoprotein(a), apo(a), which is linked to apo B by disulfide groups. The cDNA sequence of apo(a) shows a striking homology to plasminogen, with multiple repeats of kringle 4, one kringle 5, and a protease domain. The isoforms of apo(a) vary in the range of 300 to 800 kDa and differ mainly in their genetically determined number of kringle 4 structures. McLean, J. W., et al. (1987) Nature 300: 132-137. Apo(a) has no plasmin-like protease activity. Eaton, D. L., et al., (1987) Proc. Natl Acad. Sci. USA, 84: 3224-3228. Serine protease activity, however, has been demonstrated. Salonen, E., et al. (1989) EMBO J. 8: 4035-4040. Like plasminogen, Lp(a) has been shown to bind to lysine-sepharose, immobilized fibrin and fibrinogen, and the plasminogen receptor on endothelial cells. Harpel, P. C., et al. (1989) Proc. Natl. Acad. Sci. USA 86:3847-3851; Gonzalez-Gronow, M., et al. (1989) Biochemistry 28: 2374-2377; Miles, L. et al. (1989) Nature 339: 301-302; Hajjar, K. A., et al. (1989) Nature 339: 303-305. Furthermore, Lp(a) has been demonstrated to bind to other components of the arterial wall like fibronectin and glycosaminoglycans. The nature of these bindings, however, is poorly understood.

Essentially all human blood contains lipoprotein (a); however, there can a thousand-fold range in its plasma concentration between individuals. High levels of Lp(a) are associated with a high incidence of cardiovascular disease. Armstrong, V. W., et al. (1986) Atherosclerosis 62: 249-257;Dahlen, G., et al. (1986) Circulation 74: 758-765; Miles, L. A., et al. (1989) Nature 339: 301-302; Zenker, G., et al. (1986) Stroke 17: 942-945 (The term cardiovascular disease will be used hereafter as including all pathological states leading to a narrowing and/or occlusion of blood vessels throughout the body, but particularly atherosclerosis, thrombosis and other related pathological states, especially as occurs in the arteries of the heart muscle and the brain.)

It has also been suggested that Lp(a), the concentration of which increases markedly in the blood during pregnancy, may be linked to cardiovascular disease in woman. Zechner, R., et al. (1986) Metabolism 35: 333-336. It has also been observed that diabetics, many of whom suffer in some degree from atherosclerotic diseases, display greatly elevated serum levels of Lp(a). Bruckert, E., et al. (1990) JAMA 263: 35-36.

Low levels of ascorbate have also been associated with high incidences of cancer (Wright, L. C. et al. (1989) Int. J. Cancer 43: 241-244) and atherosclerosis in diabetes mellitus patients (Som, S. et al. (1981) Metabolism 30: 572-577). In all instance, serum concentrations of Lp(a) were elevated.

In addition to atherosclerosis and thrombosis in arteries Lp(a) has also been linked to stenosis of vein grafts after coronary bypass surgery. Hoff, H., et al. (1988) Circulation 77: 1238-1244. Similar problems of rapid occlusion of vessels have been observed in heart transplant patients.

For some time, general medical practice has focused on the role of LDL, the so called "bad cholesterol," in cardiovascular disease. A great many studies have been published ostensibly linking cardiovascular disease with elevated levels of LDL. As a result, most therapies for the treatment and prevention of arteriosclerosis rely on drugs and methods for the reduction of serum levels of LDLS. Such therapies have had mixed results. The efficacy of such approaches to the problem of cardiovascular disease continues to be major source of debate.

There exists a need, therefore, for a drug and therapy for reducing the binding of Lp(a) to vessel walls, for reducing the overall level of Lp(a) in the circulatory system and for promoting the deposition of existing deposits of Lp(a) on vessel walls.

SUMMARY OF THE INVENTION

The foregoing needs in the treatment and prevention of cardiovascular disease are met by the methods and compositions of the present invention.

A method is provided for the treatment of cardiovascular disease, particularly atherosclerosis, induced or promoted by kidney failure, diabetes, transplant surgery and the like, comprising the step of administering to a subject an effective amount of ascorbate and one or more binding inhibitors, as a mixture or as a compound comprising ascorbate covalently linked with binding inhibitors, which inhibit the binding of Lp(a) to blood vessel walls, such as arterial walls and vein grafts used in by-pass surgery. This effect may also be obtained by administering an effective amount of one or more inhibitors, without ascorbate. The term binding inhibitor throughout the specification and claims is intended to include all substances that have an affinity for the lysine binding site present on the interior walls of blood vessels, particularly arteries, the site of Lp(a) binding. Most of these substances compete with plasmin for the lysine binding site and some of these compounds, in high doses, are in clinical use for the treatment of hyperfibrinolytic states.

A method is further provided for the prevention of atherosclerosis related to or as a complication of surgery, a preexisting disease or a therapy such as hemodialysis. comprising the step of administering to a subject an effective amount of ascorbate and one or more binding inhibitors as previously discussed but further comprising one or more antioxidants. The term antioxidant throughout the specification and the claims is intended to exclude ascorbate, which itself is a powerful antioxidant.

It is thus an object of the invention to provide a method for treatment of induced cardiovascular disease by administering to a subject an effective amount of ascorbate and one or more binding inhibitors, or an effective amount of one or a mixture of binding inhibitors.

It is another object of the invention to provide a method for prevention of induced cardiovascular disease, by administering to a subject an amount of ascorbate effective to lower the amount of Lp(a) in the plasma of the subject.

Yet another object of the present invention is to provide a method for prevention of induced cardiovascular disease by administering to a subject an effective amount of ascorbate and one or more binding inhibitors, or an effective amount of one or more binding inhibitors.

A further object of the present invention is to provide a pharmaceutically acceptable agent for the treatment of induced cardiovascular disease.

Still another object of the present invention is to provide a pharmaceutically acceptable agent for the prevention of induced cardiovascular disease.

Yet another object of the present invention is to provide a method for preservation of explanted tissues and organs that reduces the risk of occurrence of cardiovascular disease in the tissues and organs after implantation.

It is also an object of the present invention to provide a pharmaceutically acceptable agent to assist in the preservation of explanted tissues and organs prior to implantation.

Still another object of the present invention is to provide a pharmaceutical compound and method for treating cardiovascular disease arising from a preexisting condition of diabetes mellitus.

These and other objects will be more readily understood upon consideration of the following detailed descriptions of embodiments of the invention and the drawings.

DETAILED DESCRIPTION OF THE INVENTION

Our invention is based in part on our discovery that animals which have lost the ability to produce ascorbate, such as higher primates and guinea pigs, uniformly produce Lp(a), whereas most animals which possess the ability to synthesize ascorbate generally do not produce Lp(a). Further, we have found that ascorbate deficiency in humans and guinea pigs tends to raise Lp(a) levels and causes atherosclerosis by the deposition of Lp(a) in the arterial wall, from which we conclude that ascorbate administration lowers plasma Lp(a) levels.

We have also discovered that substances that inhibit the binding of Lp(a) to components of the arterial wall, particularly to fibrinogen, fibrin and fibrin degradation products herein identified as binding inhibitors, such as lysine or ε-aminocaproic acid. Thus, ascorbate and such binding inhibitors are not only useful for the prevention of cardiovascular disease, but also for the treatment of such disease.

Figure 2:
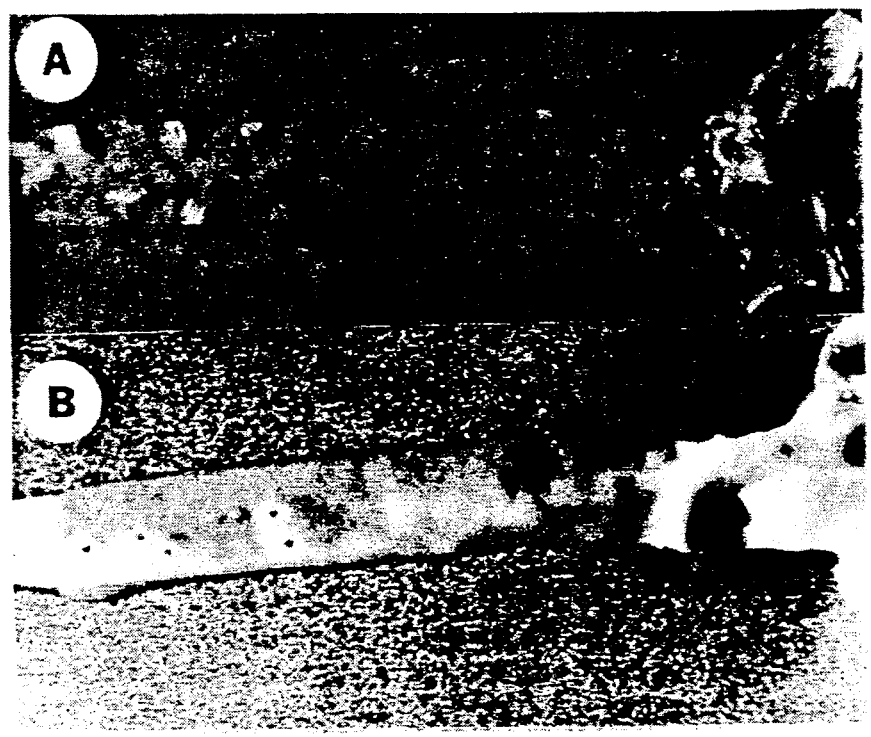
FIG. 2A is a photograph of the aorta of a guinea pig receiving an adequate amount of ascorbate from the test diet in Example 1.
FIG. 2B is a photograph of an aorta of a guinea pig receiving a hypoascorbic diet after three weeks from the test diet in Example 1.
Figure 3:
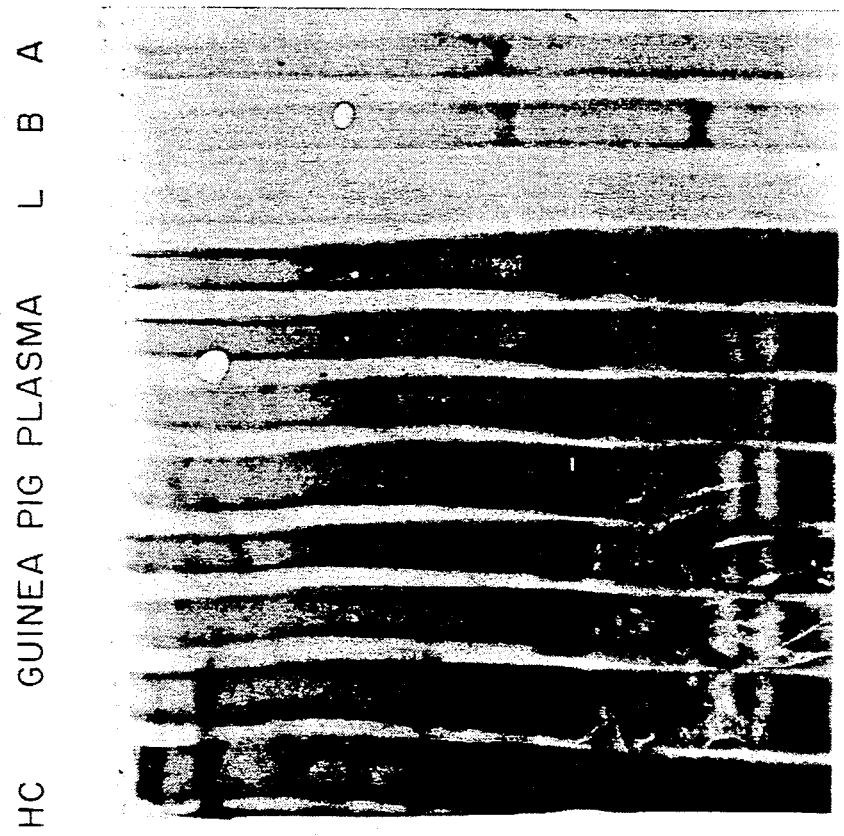
FIG. 3 is an immunoblot of plasma and tissue of guinea pigs from the test shown in Example 2. Plasma and tissue of guinea pigs. Immunoblot with anti apo(a) antibody. HC: human control plasma; L: liver tissue; B: brain tissue; A: aortic tissue, homogenate of plaque area from FIG. 2B.
Figure 4:
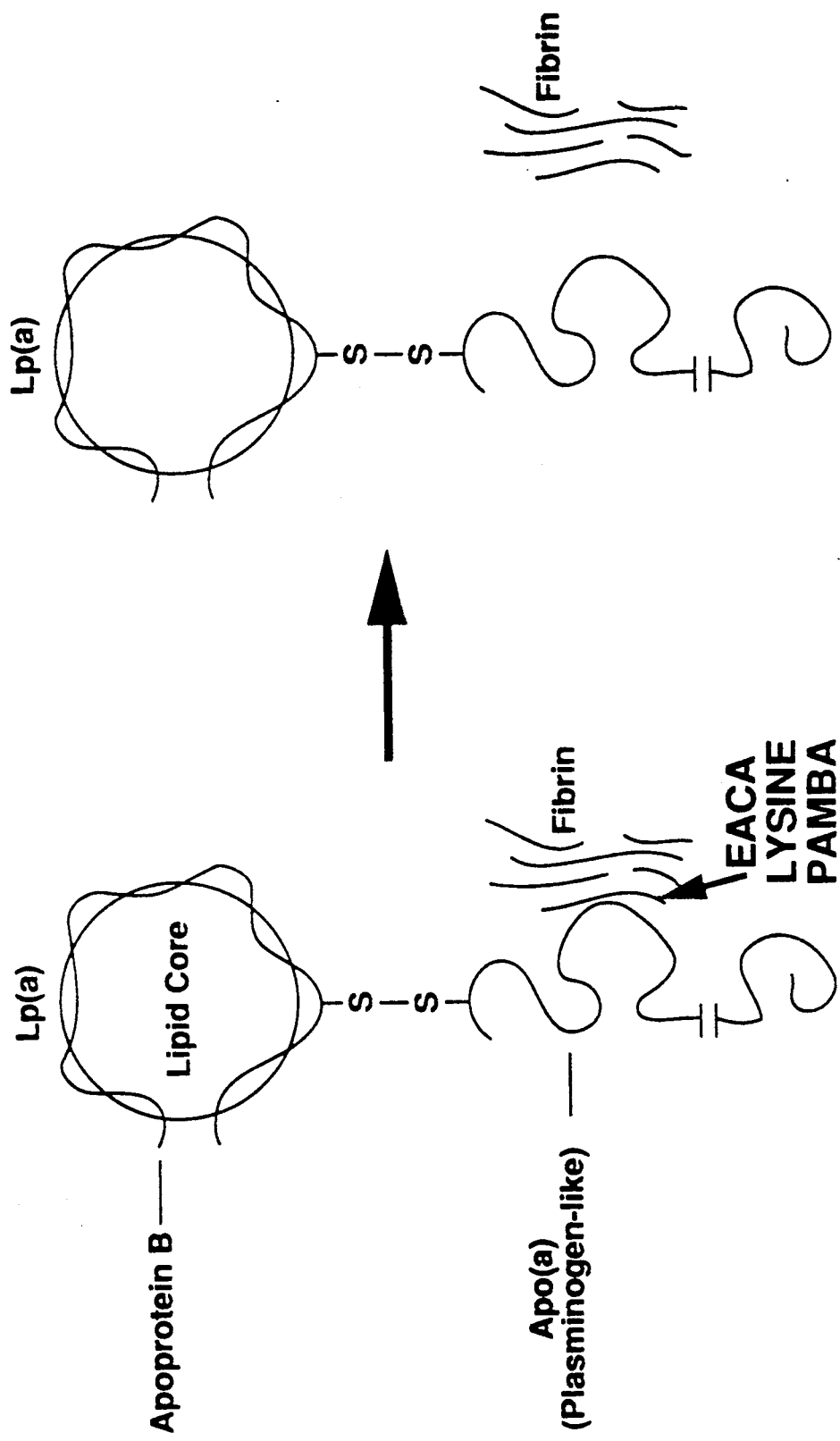
FIG. 4 is a diagrammatic representation of the action of Lp(a) binding inhibitors on Lp(a) to cause release of Lp(a) from fibrin fibers of an arterial wall.
Figure 5:
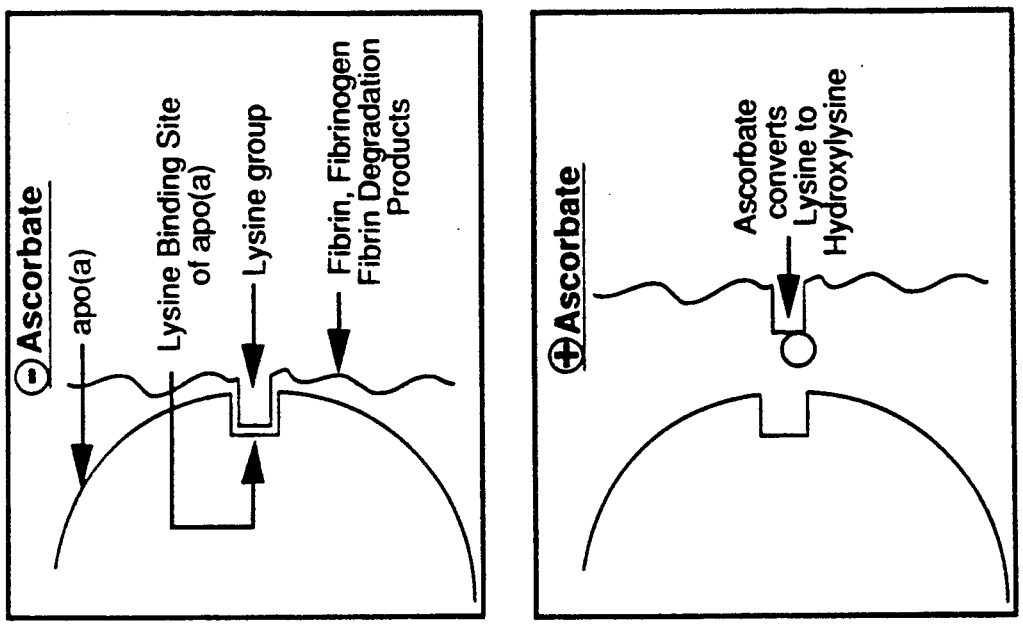
FIG. 5 is a diagrammatic representation of the action of ascorbate to prevent association and reassociation of Lp(a) to an arterial wall.
Figure 5:
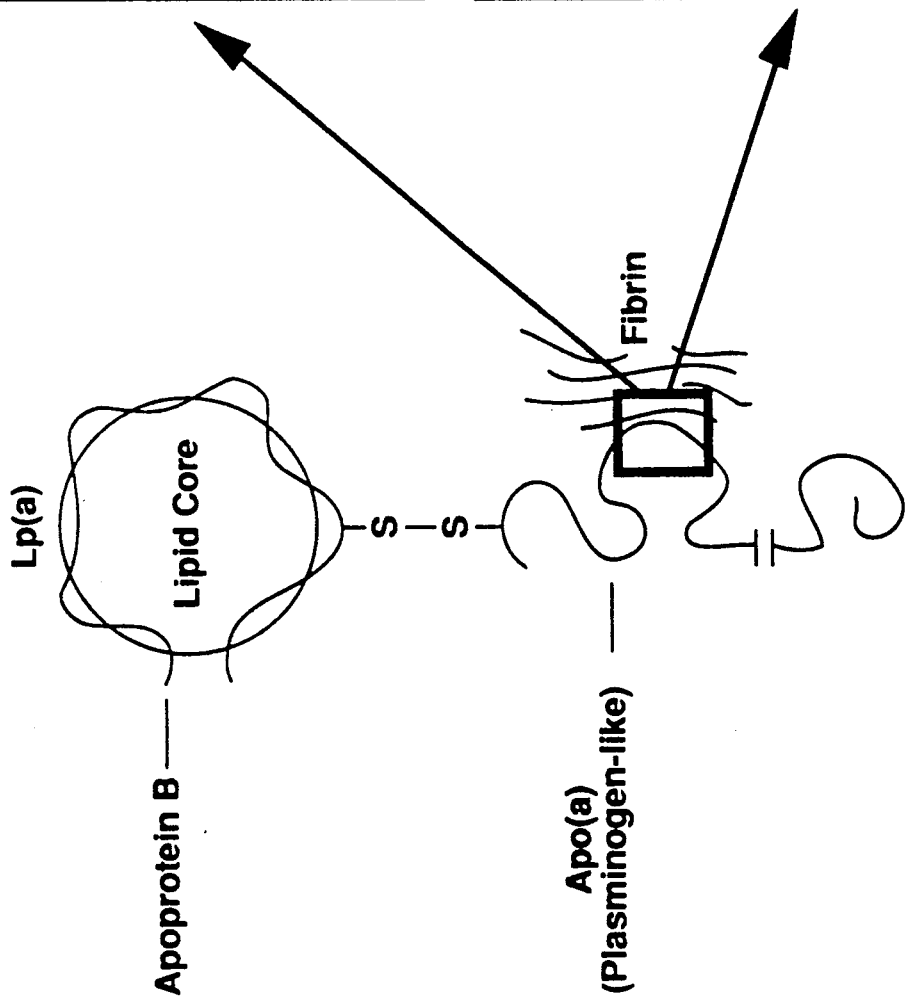

Some beneficial effects of ascorbate in the prevention and treatment of cardiovascular disease have been established (see FIG. 2). Our invention reveals the relation to and therapeutic use of ascorbate for Lp(a), one of the most atherogenic lipoproteins, directly related to the development of atherosclerotic plaques. The beneficial effects of ascorbate suggest that ascorbate therapies would be useful in a variety of situations where occlusion of blood vessels by Lp(a) deposition is a problem. For instance, ascorbate may be useful in transplantation of blood vessels and whole organs, where a combination of tissue damage to the transplant, such as by oxidation, and high serum Lp(a) in the transplant recipient results in rapid occlusion of blood vessels in the transplant. Ascorbate may also be useful in the area of hemodialysis, where loss of ascorbate and other vitamins and trace elements from the blood of hemodialysis patients can result in increased serum levels of Lp(a) and thus increased risk of cardiovascular disease. Finally, it appears that ascorbate alone and in combination with binding inhibitors, specifically with plasmin competitors, may be therapeutically useful for treatment of the pathogenic effects of diabetes which is associated with elevated serum concentrations of Lp(a).

The present invention provides methods and pharmaceutical agents for both the treatment and prevention of cardiovascular disease in vivo; methods and agents for the preservation of damage linked vessel occlusion in explanted tissues and organs, as well as methods and agents for the prevention of hemodialysis-linked cardiovascular disease. Each of these embodiments is discussed in turn below.

GENERAL APPLICATIONS

The present invention provides a method and pharmaceutical agent for the treatment and prevention of cardiovascular disease generally, particularly atherosclerosis, by administering to a subject an effective amount of ascorbate and one or more binding inhibitors which inhibit the binding of Lp(a) to blood vessel wall components, particularly to fibrin or fibrinogen. As used herein, the term "ascorbate" includes any pharmaceutically acceptable salt of ascorbate, including sodium ascorbate, as well as ascorbic acid itself. Binding inhibitors include, but are not limited to ε-aminocaproic acid (EACA), lysine, tranexamic acid (4-aminomethylcyclohexane carboxylic acid), p-aminomethylbenzoic acid, p-benzylamine sulfuric acid, and α-N-acetyl-lysine-methyl ester and PROBUCOL (a compound comprised of 2 butyl hydroxy tocopherol groups linked together by a disulphide group), Aprotinin, trans-4-aminomethylcyclohexanecarboxylic acid (AMCA), and benzamidine derivatives such as amidinophenylpyruvic acid (APPA) and 1-naphthyl-(1)-3-(6-amidinonaphthyl-(2))-propanone-1 HCl (NANP). An effective amount of a binding inhibitor or a mixture of binding inhibitors may also be used, without ascorbate. Other substances used in the treatment of cardiovascular disease may be co-administered, including: antioxidants, such as tocopherol, carotene and related substances; vitamins; provitamins; trace elements; lipid-lowering drugs, such as hydroxy-methyl-glutaryl coenzyme A reductase inhibitors, nicotinic acid, fibrates, bile acid sequestrants; and mixtures of any two or more of these substances.

Although ascorbate can be used alone or in varying combinations with one or more representative constituents of the above classes of compounds, we prefer when treating a pre-existing cardiovascular condition to combine ascorbate with at least one each of the binding inhibitors, antioxidants and lipid lowering drugs elements in the dosages (per kilogram of body weight per day (kg BW/d)) provided in Table 1. It should be noted that Table 1 provides differing concentration ranges of each constituent, depending upon whether the agent is to be administered orally or parenterally. The variance in dosages is reflective of variation in disease severity. It will be realized therefore that if the subject has been diagnosed for advanced stages of atherosclerosis, dosages at the higher end of this range can be utilized. However, if only prevention of an atherosclerosis condition is the object, dosages at the lower end of this range can be utilized.

As an alternative, a pharmaceutical agent identical to the one just described, but omitting ascorbate, may be employed.

Where ascorbate and binding inhibitors are utilized in the same agent, they may simply be mixed or may be chemically combined using synthesis methods well known in the art, such as compounds in which ascorbate and the inhibitor are covalently linked, or form ionically bound salts. For example, ascorbate may be bound covalently to lysine, other amino acids, or ε-aminocaproic acid by ester linkages. Ascorbyl ε-aminocaproate is such an example. In this form the ascorbate moiety may be particularly effective in preventing undesirable lipid peroxidation.

In the case of oral administration, a pharmaceutically acceptable and otherwise inert carrier may be employed. Thus, when administered orally, the active ingredients may be administered in tablet form. The tablet may contain a binder such as tragacanth, corn starch or gelatin; a disintegrating agent, such as alginic acid, and/or a lubricant such as magnesium stearate. If administration in liquid form is desired, sweetening and/or flavoring agents may be used. If administration is by parenteral injection, in isotonic saline, a phosphate buffered solution or the like, may be used as pharmaceutically acceptable carrier.

The advisability of using binding inhibitors in treating cardiovascular disease will depend to some extent on the subject's general health, particularly with regard to hyperfibrinolytic conditions. Most binding inhibitors (except lysine) are used clinically to treat such conditions. As a result, monitoring of the subject's coagulation and fibrinolytic system is recommended before and during treatment for cardiovascular disease. Long-term administration of binding inhibitors will require formulations in which the dosages of binding inhibitors are in the lower ranges of the dosages given in Table 1.

Prevention, as contrasted with treatment, of cardiovascular disease may be accomplished by oral or parenteral administration of ascorbate alone. Table 1 gives a range of ascorbate concentrations sufficient to lower the serum Lp(a) concentration. Preferably the prevention of the cardiovascular disease according to the invention is accomplished by use of a physical mixture of ascorbate and one or more binding inhibitors, or by use of a compound comprising covalently linked ascorbate with one or more of the binding inhibitors, which inhibit binding of Lp(a) to the arterial wall. A binding inhibitor or mixture of binding inhibitors may also be administered without ascorbate to prevent Lp(a)-associated cardiovascular disease.

To optimize the therapeutic effect of the release of Lp(a) from the blood vessel walls, the ascorbate and the binding inhibitors described above may be separately administered. Further optimization of therapeutic effect can be gained by using a time release composition to achieve relatively constant serum concentrations of the agent through time.

CORONARY BYPASS APPLICATIONS

As discussed above, recurrence of cardiovascular disease after bypass surgery is a frequent problem. Physicians often observe that the veins used to replace occluded arteries become rapidly occluded themselves after implantation, often requiring the patient to undergo successive surgical episodes to replace clogged bypasses. While not wishing to be bound to any theory, we believe that the rapid occlusion observed in many individual's results from a combination of the patient's pre-existing elevated levels of Lp(a) and injury to the bypass veins, during transplantation, particularly as a result of oxidative damage during explantation. This damage makes binding of Lp(a) to the vessel interior easier. Further, Lp(a) has been detected in abundance in reoccluded by-pass veins after coronary bypass surgery. See, Cushing, et al. (1989) Atherosclerosis 9:593-603. Lp(a) is now known to be the most significant factor for reocclusion of bypass veins. See, Hoff, H, et al. (1988) Circulation 77:1238-1244. Thus, a further embodiment of this invention includes using the pharmaceutical agent of the present invention to lower the bypass patient's Lp(a) before, during and after surgery while at the same using a solution containing the agent to rinse and store the bypass veins until such time as the veins are implanted into the recipient, thereby reducing oxidative damage that can make Lp(a) binding more likely after implantation.

The treatment protocols for the bypass patient generally follow those described above for the treatment of pre-existing cardiovascular disease. The composition of the pharmaceutical agent will generally include ascorbate, one or more binding inhibitors, one or more antioxidants and one or more lipid lowering drugs as enumerated and in the dosages given in Table 1. Of course, the level of dosage will depend on disease severity. Further, the constituents of the agent can be combined just as described above, can be administered either orally or parenterally and can be combined with a pharmaceutically acceptable carrier.

TABLE 1
DOSAGES OF COMPONENTS IN THE DRUG COMPOSITIONS OF THE PRESENT INVENTION

| | Oral Administration | Parenteral Administration |
|---|---|---|
| Ascorbate: | 5 mg–2500 mg/kg bw/d | 25 mg–2500 mg/kg bw/d |
| Binding inhibitors: | | |
| EACA | 5 mg–500 mg/kg bw/d | same |
| Tranexamic Acid | 1 mg–100 mg/kg bw/d | same |
| Para-aminomethyl benzoic acid | 1 mg–30 mg/kg bw/d | same |
| Lysine | 5–500 mg/kg bw/d | same |
| Antioxidants: | | |
| Tocopherol | 0,1 IU–20 IU/kg bw/d | same |
| Carotene | 100 IU–1000 IU/kg bw/d | same |
| Lipid Lowering Drugs: | | |
| Nicotinic Acid | 1 mg–300 mg/kg bw/d | |
| HMG-CoA | 0.1–10 mg/kg bw/d | |
| Fibrates | 0.1–20 mg/kg bw/d | |
| Probucol | 0.1–20 mg/kg bw/d | |
| Bile Acid Sequestrants | 10–400 mg/kg bw/d | |

Turning now to vessel treatment and storage, it is important to provide an in vitro environment which minimizes vessel injury. We conclude that vessel injury can be reduced by the addition of a combination of ascorbate, binding inhibitors and antioxidants to the solution in which the vessels are normally stored. A range of effective concentrations of these constituents in solution is given in Table 2. The general aspects of live vessel preservation and storage prior to implantation are well known in the art.

TABLE 2
CONCENTRATION OF COMPONENTS IN THE SOLUTION OF THE PRESENT INVENTION

| | |
|---|---|
| Ascorbate | 50–5000 mg/l |
| Binding Inhibitors: | |
| EACA | 2–2000 mg/l |
| Tranexamic Acid | 1–300 mg/l |
| Para-aminomethyl benzoic acid | 1–200 mg/l |
| Lysine | 10–5000 mg/l |
| Antioxidants | |
| Tocopherol | 1–1000 mg/l |
| Carotene | 0.1–100 mg/l |

APPLICATIONS IN ORGAN TRANSPLANTS

We have also found that the solution and method of the present invention are effective in preventing cardiovascular disease from occurring in transplanted organs that have been otherwise successfully implanted in an organ recipient, particularly in the case of the heart.

As with occlusion of transplanted veins after bypass surgery, a transplanted heart free of any substantial arterial occlusion may suffer accelerated atherosclerosis after implantation. We believe that the mechanism described for occlusion of transplanted vessels applies equally to the heart itself as a whole, namely that the heart muscle itself, as well as the interiors of the arterial walls become damaged, making the arteries of the heart more prone to binding with Lp(a). Because the organ recipient often presents elevated serum concentration of Lp(a), particularly after surgery (see, Maeda, S. et al. (1989) Atherosclerosis 78: 145–150), atherosclerosis can proceed at an accelerated rate.

Treatment follows along the same line as that described for bypass surgery. Damage to the organ itself is minimized by placing the organ in a solution containing a mixture of ascorbate, binding inhibitors, and antioxidants in an otherwise standard storage solution. Concentration ranges for the various components in the final solution are given in Table 2. Because of the oxidative cellular damage during extended periods of explantation, the concentration of antioxidants should be in the higher range of dosages disclosed in Table 1. The standard storage solution itself is well known in the art. Storage of the organ in this solution will tend to minimize damage to arterial walls, thereby providing fewer places for Lp(a) to bind.

Of course, patient treatment is also desireable. If the organ recipient suffers from some degree of atherosclerosis at the time of organ transplant, the protocol and drug described above generally for the treatment of atherosclerosis should be employed. If, however, the patient does not suffer from atherosclerosis, use of the drug and protocol described above for prevention of atherosclerosis is desired. In all cases, the lowest dosages of ascorbate should be employed in the drug composition since ascorbate has an immune stimulatory effect.

APPLICATIONS IN HEMODIALYSIS TREATMENT

It is well known that patients who suffered renal failure and require regular dialysis treatment to cleanse the blood of metabolic waste products are also at an increased risk for cardiovascular disease. We believe that the reason for this may be a depletion of ascorbate, vitamins in general and other essential substances from the blood supply during the hemodialytic process. As described more fully above, the loss of ascorbate would result in greater injury to the interior of the artery walls over time and may also result in the production of elevated Lp(a) levels in the blood serum.

As can appreciated, the solution and method of the present invention can be applied both to the patient and the hemodialysis solution to prevent and control hemodialysis-related cardiovascular disease. Turning first to the hemodialysis solution, it is desired to add a combination of ascorbate, binding inhibitors and antioxidants to the solution to produce concentrations of these compounds in solution in the range of concentrations provided in Table 2.

In order to achieve the best results, treatment of the dialysis patient should be carried out in addition to modification of the hemodialysis solution. Treatment should follow the drug and protocols set forth in detail above for the treatment of a preexisting atherosclerotic condition.

APPLICATIONS IN TREATMENT OF DIABETES

The composition and method of the present invention are also useful in the treatment of the pathological effects of diabetes mellitus. In diabetes mellitus, pathological charges in the arteries frequently lead to clinical symptoms or complete failure in various organs such as the kidney, eye and peripheral circulation system. Therefore, one therapeutic focus in diabetes mellitus is the treatment of diabetic angiopathy.

It appears that glucose competitively inhibits the physiologic uptake of ascorbate in different cell systems of the body, including the arterial wall. Kapeghian, et al. (1984) Life Sci. 34: 577. Such damage to arterial walls creates binding sites for Lp(a). Further, Lp(a) has been found to be elevated in the blood serum of diabetic patients. The atherogenic process is perhaps therefore accelerated by the combination of damaged arteries and elevated Lp(a). Therefore, we propose that ascorbate alone or in combination with at least one binding inhibitor has therapeutic value in treating diabetes-related atherosclerosis.

Thus, another embodiment of the present invention is the use of a composition and method in treating the pathogenic effects of diabetes mellitus, particularly with regard to atherosclerotic conditions.

The treatment protocol involves the oral or parenteral administration of a pharmaceutical composition comprised of ascorbate, one or more binding inhibitors and one or more antioxidants. Dosages for a course of treatment are provided in Table 1. The dosage of ascorbate should preferably fall within the higher range, thereby increasing its chance of cellular uptake in the presence of high serum levels of glucose.

EXPERIMENTAL

Having disclosed the preferred embodiment of the present invention, the following examples are provided by way of illustration only and are not intended to limit the invention in any way.

EXAMPLE 1

Because of its metabolic similarity to man, with respect to the metabolism of ascorbate and Lp(a), the guinea pig was used in this example.

No study has been previously reported in the guinea pig to identify the lipoprotein involved as risk factors in plasma and as constituents of the atherosclerotic plaque.

Three female Hartly guinea pigs with an average weight of 800 g and an approximate age of 1 year were studied. One animal received an extreme hypoascorbic diet with 1 mg ascorbate/kg body weight/d. Another animal received 4 mg/k BW/d. The third animal served as a control receiving 40 mg ascorbate/Kg BW/d.

Blood was drawn by heart puncture from the anesthetized animals and collected into EDTA containing tubes at the beginning, after 10 days, and after 3 weeks, when the animals were sacrificed. Plasma was stored at −80° C. until analyzed. Lp(a) was detected in the plasma of the guinea pigs by use of SDS-polyacrylamide gels according to Neville (J. Biol. Chem., 246, 6328–6334 (1971)) followed by Western blotting (Beisiegel, et al., J.Biol. Chem., 257, 13150–13156 (1982)). 40 μl of plasma and 20 mg of arterial wall homogenate were applied in delipidated form per lane of the gel. The immunodetection of apo(a) was performed using a polyclonal anti-human apo(a) antibody (Immuno, Vienna, Austria) followed by a rabbit anti-sheep antibody (Sigma) and the gold-conjugated goat anti-rabbit antibody with subsequent silver enhancement (Bio-Rad). The determinations of cholesterol and triglycerides were done at California Veterinary Diagnostics (Sacramento) using the enzyme assay of Boehringer Mannheim. Plasma ascorbate was determined by the dinitrophenylhydrazine method (Schaffer, et al., J. Biol. Chem., 212, 59 (1955)).

Figure 1:
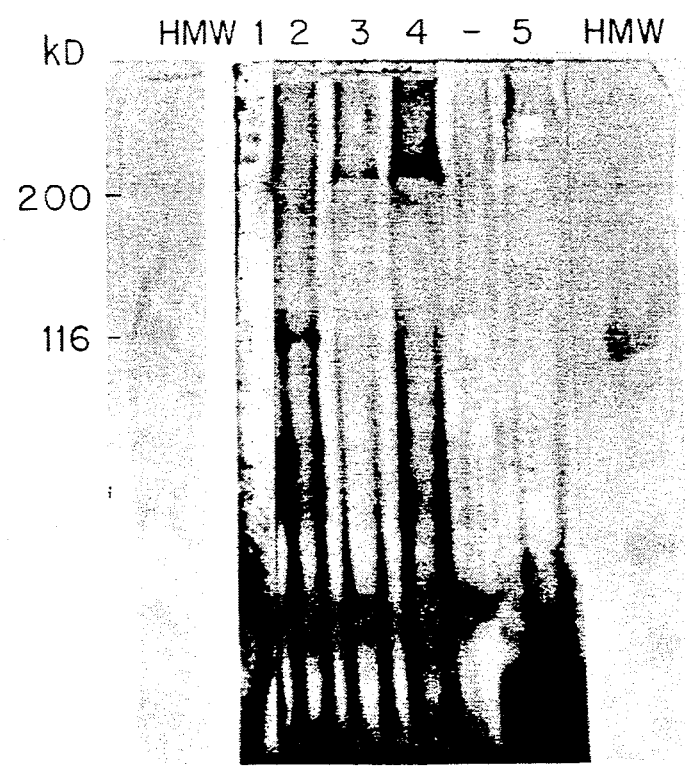
FIG. 1 is an immunoblot of the plasma of guinea pigs from the test described in Example 1. Increase of Lp(a) in plasma of guinea pigs with a hypoascorbic diet. Immuunoblot with anti apo(a) antibodies. Lane 1: human control plasma. Lane 2: guinea pig plasma at the start of experiment. Lane 3: guinea pig plasma after 10 days of hypoascorbic diet. Lane 4: guinea pig plasma after 20 days. HMW: high molecular weight standard.

Vitamin C deficiency in the diet led to an increase of Lp(a) in the plasma of the guinea pig indicated by a clear band in the immunoblot of the plasma after 10 and 20 days of a hypoascorbic diet (FIG. 1). At necropsy the animals were anesthetized with metophase and were exsanguinated. Aorta, heart and various other organs were taken for biochemical and histological analysis. The aorta was excised, the adventitial fat was carefully removed, and the vessel was opened longitudinally. Subsequently the aorta was placed on a dark metric paper and a color slide was taken. The picture was projected and thereby magnified by an approximate factor 10. The circumference of the ascending aorta, the aortic arch and thoracic aorta as well as the atherosclerotic lesions in this area were marked and measured with a digitalized planimetry system. The degree of atherosclerosis was expressed by the ratio of plaque area to the total aortic area defined. The difference in the 3 one-year old animals of the experiment was significant and pronounced lesions were observed in the ascending aorta and the arch of the vitamin C deficient animal (FIG. 2B).

EXAMPLE 2

To confirm the data obtained in Example 1, a second guinea pig experiment was conducted, using 33 male animals with a mean weight of 550 g and an approximate age of 5 months. One group of 8 animals served as a control and received 40 mg ascorbate/kg BW/d (group A). To induce hypoascorbemia 16 animals were fed 2 mg ascorbate/kd/d (group B). Group A and half of the animals of group B (progression sub-group) were sacrificed after 5 weeks as described above. Half of group B was kept for 2 more weeks, receiving daily intraperitoneal injection of 1.3 Na-ascorbate/kg BW/d as a daily intra peritoneal injection with the intention to reduce the extent of atherosclerosis lesions. After this period these animals also were sacrificed.

Plasma ascorbate levels were negatively correlated with the degree of the atherosclerotic lesion. Total cholesterol levels increased significantly during ascorbic acid deficiency (Table 3).

The aortas of the guinea pigs receiving a sufficient amount of ascorbate were essentially plaque free, with minimal thickening of the intima in the ascending region. In contrast, the ascorbate-deficient animals exhibited fatty streak-like lesions, covering most parts of the ascending aorta and the aortic arch. In most cases the branching regions of the intercostal arteries of the aorta exhibited similar lipid deposits. The difference in the percentage of lesion area between the control animals and the hypoascorbic diet animals was 25% deposition of lipids and lipoproteins in the arterial wall.

TABLE 3

MEAN PLASMA PARAMETERS OF THE DIFFERENT GROUPS IN RELATION TO THE AREA OF AORTIC LESIONS

|  | Control | Scurvy (progress) | Regression (after Scurvy) |
|---|---|---|---|
| Plasma Cholesterol (mg/dl) | 39 | 54 | 33 |
| Total Plasma Ascorbic Acid µg/ml | 5.03 | 3.01 | 20.64 |
| Atheroscl. Lesion (Percent of Aorta Thorac. Surface) | — | 25 | 19 |

A possible inhibitor may be identified first by adding molar amounts of the possible inhibitor at a little larger, by approximately 5 times, the amount of ε-aminocaproic acid found in the earlier study. If, at this concentration, a possible inhibitor is found to inhibit the agglutination, studies are made at lower concentrations, to determine the concentration that has a 50% initiatory effect.

EXAMPLE 3

Human arterial wall was obtained post mortem from the aorta ascendens. The tissue showed homogenous intimal thickening (early atherosclerotic lesion). It was cut into pieces, with 100 mg of the cut up tissue homogenized in a glass potter for 1 minute in 2.5 ml of the following solutions:

| PBS (Dulbeco) + NaAscorbate | 50 mg/ml |
|---|---|
| PBS + EACS | 50 mg/ml |
| PBS + Tranexamic Acid | 50 mg/ml |
| PBS + NaAscorbate + Tranexamic Acid | 50 mg/ml |

Results of this treatment are given in Table 4 and show that, compared to the control solution, a considerable amount of Lp(a) was released from the interior arterial wall.

TABLE 4

Lp(a) RELEASED FROM HUMAN AORTA IN RELATION TO SPECIFIC BINDING INHIBITORS

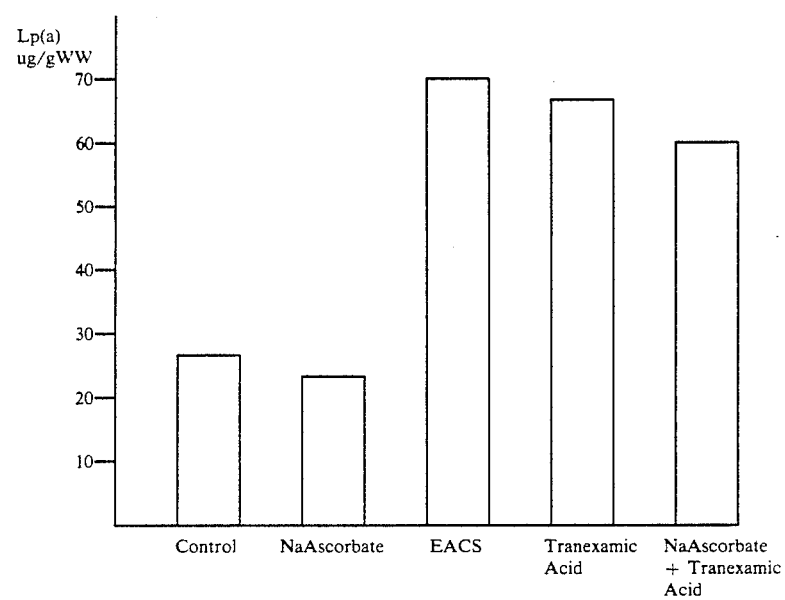

By now it is apparent that the methods and compositions of the present invention meet longstanding needs in the field of prevention and treatment of induced cardiovascular disease. Although preferred embodiments and examples have been disclosed, it is understood that the invention is in no way limited thereby, but rather is defined by the claims that follow and the equivalents thereof.

What is claimed is:

1. A method for reducing lipoprotein(a) binding to vessel explants prior to implantation comprising the step of storing the vessel explants in an aqueous composition comprising ascorbate and tranexamic acid in concentrations sufficient to decrease binding of lipoprotein(a) to interior walls of the vessel explants.

2. A method according to claim 1 wherein said ascorbate is selected from the group consisting of pharmaceutically acceptable ascorbate salts, ascorbic acid and mixtures thereof.

3. A method according to claim 2 wherein said ascorbate is covalently linked to said tranexamic acid.

4. A method for reducing injury to organ explants prior to implantation comprising the step of storing the organ explants in an aqueous composition comprising ascorbate and tranexamic acid in concentrations sufficient to decrease binding of lipoprotein(a) to interior walls of vessels within the organ explants.

5. A method according to claim 4 wherein said ascorbate is selected from the group consisting of pharmaceutically acceptable ascorbate salts, ascorbic acid and mixtures thereof.

6. A method according to claim 5 wherein said ascorbate is covalently linked to said tranexamic acid.

7. A method according to either claim 4 or 5 wherein said composition is a pharmaceutical composition administered in an amount effective to release at least some of the vessel-bound lipoprotein(a).

8. A method for reducing lipoprotein(a) binding to organ explants prior to implantation comprising the step of storing the organ explants in an aqueous composition comprising ascorbate and tranexamic acid in concentrations sufficient to decrease lipoprotein(a) binding to interior walls of vessels within the organ explants.

* * * * *